United States Patent

Baker et al.

[11] Patent Number: 6,040,487
[45] Date of Patent: Mar. 21, 2000

[54] PROCESS FOR THE MANUFACTURE OF HALOCARBONS

[75] Inventors: Ralph Thomas Baker, Los Alamos, N.Mex.; Viacheslav Alexandrovich Petrov, Hockessin; Velliyurnott Mallikarjuna Rao, Wilmington, both of Del.

[73] Assignee: E. I. du Pont de Nemours and Company, Wilmington, Del.

[21] Appl. No.: 09/011,402

[22] PCT Filed: Jul. 31, 1996

[86] PCT No.: PCT/US96/12548

§ 371 Date: Jan. 28, 1998

§ 102(e) Date: Jan. 28, 1998

[87] PCT Pub. No.: WO97/05090

PCT Pub. Date: Feb. 13, 1997

Related U.S. Application Data

[60] Provisional application No. 60/001,702, Aug. 1, 1995.

[51] Int. Cl.[7] .......................... C07C 21/18; C07C 17/32; C07C 255/00; C07C 69/63
[52] U.S. Cl. ......................... 570/172; 570/257; 558/357; 558/370; 560/226; 560/227
[58] Field of Search ..................................... 570/172, 257; 560/226, 227; 558/357, 370

[56] References Cited

U.S. PATENT DOCUMENTS

| | | | |
|---|---|---|---|
| 5,446,217 | 8/1995 | Van Der Puy | 570/156 |
| 5,574,192 | 11/1996 | VanDerPuy et al. | 570/167 |

FOREIGN PATENT DOCUMENTS

| | | |
|---|---|---|
| 2 073 533 | 1/1993 | Canada. |
| 2 188 929 | 10/1987 | United Kingdom. |
| WO 95/04021 | 2/1995 | WIPO. |
| WO 95/04022 | 2/1995 | WIPO. |
| WO 97/05089 | 2/1997 | WIPO. |

*Primary Examiner*—Alan Siegel

[57] ABSTRACT

A liquid phase process is disclosed for producing halogenated alkane adducts of the formula: $CAR^1R^2CBR^3R^4$ (where, A, B, $R^1$, $R^2$, $R^3$ and $R^4$ are defined in the specification) which involves contacting a corresponding halogenated alkane, AB, with a corresponding olefin, $CR^1R^2=CR^3R^4$, in the presence of a catalyst system containing (i) at least one catalyst selected from monovalent and divalent copper, and (ii) a promoter selected from aromatic or aliphatic hetercyclic compounds which contain at least one carbon-nitrogen double bond in the heterocyclic ring. When hydrochlorofluorocarbons are formed, hydrofluorocarbons may be formed therefrom by reacting the hydrochlorofluorocarbons with HF.

19 Claims, No Drawings

PROCESS FOR THE MANUFACTURE OF HALOCARBONS

This application is a national filing under 35 USC 371 of International Application No. PCT/US96/12548 filed Jul. 31, 1996, which claims priority of U.S. Provisional Application No. 60/001,702 filed Aug. 1, 1995.

FIELD OF THE INVENTION

This invention relates to a process for the manufacture of halogenated alkanes by the catalytic reaction of haloalkanes with halogenated olefins.

BACKGROUND

The catalyzed radical addition of haloalkanes to olefins is a well known reaction. Typically, however, when a haloalkane (e.g., AB, where A is a substituted carbon atom and B is a halogen other than fluorine) is added to an olefin (e.g., $CH_2=CHR$) to form the saturated adduct (e.g., $CH_2ACHBR$), the products (i.e., halogenated addition compounds) also include varying amounts of telomers (e.g., $A(CH_2CHR)_nB$, where n is equal to 2 or more). For example, Canadian Pat. No. 2,073,533 discloses a process for the manufacture of $CCl_3CH_2CCl_3$ by reacting carbon tetrachloride with vinylidene chloride using copper catalysts in acetonitrile. The selectivity for $CCl_3CH_2CCl_3$ with respect to converted vinylidene chloride was 87%. It has been shown in the art that the major by-product is the $C_5$ telomer, $CCl_3(CH_2CCl_2)_2Cl$.

The halogenated adducts are useful intermediates for the production of fluoroalkanes, particularly, hydrofluoroalkanes. These latter compounds are useful as refrigerants, fire extinguishants, heat transfer media, gaseous dielectrics, sterilant carriers, polymerization media, particulate removal fluids, carrier fluids, buffing abrasive agents, displacement drying agents, propellants, foaming agents and power cycle working fluids. There is an interest in developing more efficient processes for the manufacture of hydrofluoroalkanes.

SUMMARY OF THE INVENTION

A liquid phase process is provided in accordance with this invention for producing halogenated alkane adducts of the formula $CAR^1R^2CBR^3R^4$ wherein $R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl (e.g., phenyl), provided that only two of $R^1$, $R^2$, $R^3$, and $R^4$ can be selected from $C_1$–$C_6$ alkyl, CN, $CO_2CH_3$, $CH_2Cl$, and aryl; A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$ (e.g., $CF_3$ and $CCl_2CF_3$), each X is independently selected from the group consisting of Br, Cl and I, a is an integer from 0 to 3, n is an integer from 1 to 6, b is an integer from 1 to 2n+1, and c is an integer from 0 to 1; and B is selected from the group consisting of Br, Cl and I; provided that (1) when A is $CX_3$ then only one of X is I, (2) when A is $CH_{3-a}X_a$, then each X is B and a is an integer from 1 to 2 when B is Br, a is 2 when B is Cl, and a is an integer from 0 to 2 when B is I, and (3) when A is $C_nH_{(2n+1)-b}X_b$, then each X is independently selected from Cl and F, and B is I. The process comprises contacting a halogenated alkane of the formula AB (where A and B are as indicated above) with an olefin of the formula $CR^1R^2=CR^3R^4$ (where $R^1$, $R^2$, $R^3$ and $R^4$ are as indicated above) in the presence of a catalyst system containing (i) at least one catalyst selected from the group consisting of monovalent and divalent copper, and (ii) at least one promoter selected from the group consisting of aromatic or aliphatic heterocyclic compounds which contain at least one carbon-nitrogen double bond in the heterocyclic ring.

This invention further provides a process for producing hydrofluoroalkanes (e.g., $CF_3CH_2CHF_2$). This process comprises (a) producing a hydrochlorofluoroalkane (e.g., $CCl_3CH_2CHCl_2$) by reacting a halogenated alkane of the formula AB (e.g., $CCl_4$) and an olefin of the formula $CR^1R^2=CR^3R^4$ (e.g., $CH_2=CHCl$) as indicated above (provided that B and X are Cl and at least one of said reactants contains hydrogen), and (b) reacting the hydrochlorofluoroalkane produced in (a) with HF.

DETAILED DESCRIPTION

The present invention provides a liquid phase process for the manufacture of halogenated alkanes of the formula $CAR^1R^2CBR^3R^4$ by contacting a corresponding halogenated alkane, AB, with a corresponding olefin, $CR^1R^2=CR^3R^4$, in the presence of a copper catalyst ($Cu^+$ and/or $Cu^{++}$) and a promoter (containing a C=N ring bond).

Examples of halogenated alkanes of the formula AB, where A and B are as defined above, include, $CBrCl_3$, $CBrF_3$, $CCl_4$, $CCl_3F$, $CCl_2F_2$, $CF_3I$, $CCl_2FCCl_2F$, $CCl_3CF_3$, $CCl_3(CF_2CF_2)_qCl$ (where q is an integer from 1 to 6), $CCl_3CH_2CF_3$, $CCl_3CF_2CF_3$, $CCl_3CH_2CCl_3$, $CF_3CF_2I$ and $CF_3CF_2CF_2I$.

Examples of olefins of the formula $CR^1R^2=CR^3R^4$, where $R^1$, $R^2$, $R^3$ and $R^4$ are as defined above, include, $CF_2=CF_2$, $CF_2=CClF$, $CF_2=CCl_2$, $CClF=CClF$, $CClF=CCl_2$, $CF_2=CHF$, $CF_2=CH_2$, $CHF=CHF$, $CHF=CH_2$, $CH_2=CH_2$, $CH_2=CHCH_3$, $CH_2=CHCF_3$, $CH_2=CFCF_3$, $CH_2=CHCl$, $CH_2=CCl_2$, $CHCl=CHCl$, $CHCl=CCl_2$, $CH_2=CHCl$, $CH_2=CHCH_2Cl$, $CH_2=CHAryl$ (e.g., $CH_2=CHC_6H_5$), $CH_2=CHCO_2CH_3$, $CH_2=C(CH_3)CO_2CH_3$, $CH_2=CHCO_2C_2H_5$, and $CH_2=C(CH_3)CO_2C_2H_5$.

The addition of halogenated alkanes to alkenes (i.e., olefins) to form the corresponding adducts is catalyzed by copper compounds in the +1 or +2 oxidation state. Preferred copper compounds for the process of this invention include copper(I) chloride, copper(II) chloride, copper(I) bromide, copper(II) bromide, copper(I) iodide, copper(II)acetate and copper(II) sulfate. The catalysts are preferably anhydrous; and preferably, the addition is done under substantially anhydrous conditions in the substantial absence of oxygen. Without wishing to be bound by theory, it is believed that the effect of the catalyst is to enhance the yield of the 1:1 addition product (i.e., the adduct) of the halogenated alkanes to the alkene relative to higher molecular weight telomers that are known in the art.

Suitable promoters for use in the catalyst system include those selected from the group consisting of imidazoles, imidazolines, oxadiazoles, oxazoles, oxazolines, isoxazoles, thiazoles, thiazolines, pyrrolines, pyridines, trihydropyrimidines, pyrazoles, triazoles, triazolium salts, isothiazoles, tetrazoles, tetrazolium salts, thiadiazoles, pyridazines, pyrazines, oxazines and dihydrooxazine. Preferred promoters include those selected from the group having Formula (I) or Formula (II) as follows:

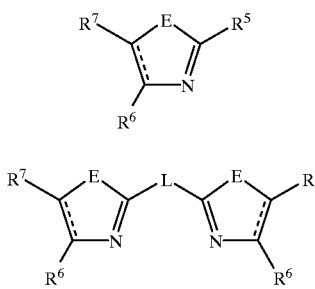

(I)

(II)

wherein E is selected from the group consisting of —O—, —S—, —Se—, —CH$_2$—, and —N(R$^8$)—; R$^5$ is selected from the group consisting of CH$_3$ and C$_2$H$_5$ (and is preferably CH$_3$); R$^6$ and R$^7$ are selected from the group consisting of H, CH$_3$, C$_6$H$_5$ (i.e., phenyl), CH$_2$C$_6$H$_5$, CH(CH$_3$)$_2$, and fused phenyl; L is selected from the group consisting of —O—, —S—, —Se—, —NR$^8$—, —C$_6$H$_4$—, 2,6-pyridyl, —OC$_6$H$_4$—C$_6$H$_4$O—, —CH$_2$CH$_2$OCH$_2$CH$_2$—, and —(CH$_2$)$_p$— where p is an integer from 0 to 6; and each R$^8$ is selected from the group consisting of H and C$_m$H$_{2m+1}$ where m is an integer from 1 to 6. The bond between each pair of carbon atoms respectively attached to R$^6$ and R$^7$ (as represented by the dashed bond lines in Formula (I) and Formula (II)) can be either a single or a double bond. Of note are compounds of Formula (II) which are optically active.

The reaction is done in the liquid phase, normally in the presence of solvents such as acetonitrile, dimethyl sulfoxide, dimethyl formamide, tetrahydrofuran, isopropanol, t-butanol, polyethers of the formula R$^9$O(CH$_2$CH$_2$O)$_r$R$^9$ where each R$^9$ is independently selected from the group consisting of H, CH$_3$ and C$_2$H$_5$ and r is an integer from 1 to 4, esters of formula R$^{10}$CO$_2$R$^{10}$ where each R$^{10}$ is independently selected from C$_1$–C$_6$ alkyl groups and mixtures thereof; acetonitrile being preferred. Also of note are systems wherein the solvent divides the reaction mixture into two liquid phases. Reference is made to U.S. Patent Application No. 60/001,702 one of the priority documents for PCT International Publication No. WO 97/05089, which is hereby incorporated by reference, for further disclosure relating to such solvent systems.

The catalyst system comprising the copper compound and promoter as disclosed above can be prepared in the solvent in advance in a suitable mixing vessel, and then added to the reaction mixture. Alternatively, the individual components of the catalyst system can be added individually to the reactor. Of note are embodiments where the reaction is accomplished in a homogeneous system (i.e., where the catalyst is dissolved).

Telomer formation can be somewhat controlled by manipulating reaction variables such as the molar ratio of halogenated alkane, AB, to olefin, CR$^1$R$^2$=CR$^3$R$^4$ or by adding the olefin to the halogenated alkane. Higher molar ratios of AB:CR$^1$R$^2$=CR$^3$R$^4$ and dilution of the olefin reduce telomer formation. However, for the addition of CCl$_4$ to CH$_2$=CCl$_2$, the highest ratio of the C$_3$ adduct CCl$_3$CH$_2$CCl$_3$ to the C$_5$ adduct was reported to be 9:1 (see Belbachir et al., Makromol. Chem.1984, 185, 1583–1595).

The amount of catalyst used in the reaction of this invention is typically at least about 5 mmol, and preferably from about 10 mmol to 100 mmol, per mole of olefin, CR$^1$R$^2$=CR$^3$R$^4$, used.

The amount of halogenated alkane starting material used in the reaction of this invention is typically at least about 1 mmol, and preferably from about 2 mmol to 10 mmol, per mmol of alkene used.

The amount of promoter used in the reaction of this invention is typically at least an amount sufficient to provide 2 mmol of heterocyclic ring which contains carbon-nitrogen double bonding per mmol of copper catalyst. For example, typically at least about 2 mmol of Formula (I) promoter or at least about 1 mmol of Formula (II) promoter, and preferably from about 4 mmol to 10 mmol of Formula (I) promoter or from about 2 mmol to 5 mmol of Formula (II) promoter is used per mmol of copper catalyst used.

The process of the present invention is suitably conducted at a temperature in the range of from about 50° C. to 150° C., preferably from about 80° C. to about 130° C.

The pressure of the process is not critical and can be subatmospheric, atmospheric or superatmospheric, preferably, superatmospheric. The reaction products may be separated by conventional techniques such as distillation.

Of note is the embodiment where AB is CCl$_4$ and CR$^1$R$^2$=CR$^3$R$^4$ is CH$_2$=CCl$_2$. The isolated 1,1,1,3,3,3-hexachloropropane adduct can then be reacted with hydrogen fluoride to produce CF$_3$CH$_2$CF$_3$ (e.g., as disclosed in U.S. Pat. No. 5,414,165).

The reaction zone and its associated feed lines, effluent lines and associated units should be constructed of materials resistant to corrosion. Typical materials of construction include steel reactors lined with poly(tetrafluoroethylene) or glass and glass reactors.

The addition compounds that comprise the products of this invention are useful as intermediates for the formation of hydrofluoroalkanes. These addition compounds can be reacted with hydrogen fluoride in either the liquid or vapor phase in the presence of a suitable fluorination catalyst.

In the liquid phase, the addition compounds can be reacted with HF in the presence of catalysts selected from the halides of antimony, molybdenum, niobium, tantalum, tin and titanium, and mixtures thereof, preferably, antimony, niobium and tantalum. The temperature of the reaction can be in the range of 50° C. to 175° C., preferably, 60° C. to 150° C. The pressure is selected so that the reaction medium is maintained in the liquid state, typically between 101 kPa and 5000 kPa, preferably, 1135 kPa to 3203 kPa. For example, 1,1,1,3,3,3-hexachloropropane (HCC-230fa) can be reacted with HF in the liquid phase using halides, fluorosulfonates or triflates of antimony, molybdenum, niobium, tantalum, tin or titanium, or mixtures thereof as catalysts to produce 1,1,1,3,3,3-hexafluoropropane (HFC-236fa). 1-Chloro-1,1,3,3,3-pentafluoropropane (HCFC-235fa) can also be prepared from HCC-230fa. HCFC-235fa can be hydrodechlorinated using a hydrodehalogenation catalyst to produce 1,1,1,3,3-pentafluoropropane (HFC-245fa). Palladium on acid-washed carbon is a preferred catalyst for the coversion of HCFC-235fa to HFC-245fa.

In another embodiment of this invention carbon tetrachloride can be reacted with vinyl chloride to produce the adduct 1,1,1,3,3-pentachloropropane (i.e., CCl$_3$CH$_2$CHCl$_2$ or HCC-240fa). CCl$_3$CH$_2$CHCl$_2$ can then be reacted with HF in the liquid phase using the process described above to produce CF$_3$CH$_2$CHF$_2$. The reaction products may be separated by conventional techniques such as distillation. Hydrofluorocarbons such as CF$_3$CH$_2$CHF$_2$ likely form azeotropes with HF; and conventional decantation/ distillation may be employed if further purification of the hydrofluorocarbons is desired.

In the vapor phase, the addition compounds can be reacted with HF in the presence of catalysts comprising trivalent chomium. Catalysts prepared by pyrolysis of (NH$_4$)$_2$Cr$_2$O$_7$ to produce $Cr_2O_3$ and pretreated with HF and catalysts prepared by pretreating $Cr_2O_3$ having a surface area greater than about 200 m²/g with HF are preferred. The temperature of the reaction can be in the range of 200° C. to 400° C., preferably, 250° C. to 375° C. The pressure is not critical and is selected so that the reaction starting materials and products are maintained in the vapor state at the operating temperature. For example, it has recently been disclosed in U.S. Pat. No. 5,414,165 that 1,1,1,3,3,3-hexafluoropropane may be prepared in high yield from 1,1,1,3,3,3-hexachloropropane by a vapor phase hydrofluorination process in the presence of a trivalent chromium catalyst.

Although the 1:1 addition compounds of the halogenated alkanes to the alkenes are the preferred products, the 2:1 adducts may also be useful intermediates.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLE 1

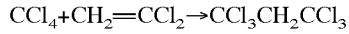

A suspension of 10 mg (0.1 mmol) CuCl in 4 mL of MeCN was treated with 2 equivalents of the promoter (i.e., ligand), except where noted otherwise, 114 mg of n-octane internal standard and 100 mg (1 mmol) of $CH_2=CCl_2$. To this mixture was added 1.54 g (10 mmol) $CCl_4$. The glass reaction vessel was then pressurized with 200 psi (1480 kPa) $N_2$ and heated at 100° C. for 2 hr. The reaction mixture was analyzed by GC; results are summarized in Table 1, where % conversion is the molar % conversion of vinylidene chloride (i.e., $CH_2=CCl_2$), $C_3:C_5$ is the molar ratio of $CCl_3CH_2CCl_3$ to $CCl_3CH_2CCl_2CH_2CCl_3$, and the ligands used are shown in the Legend; monodentate ligands are numbered 1–12 and bidentates are labeled with letters A–F.

LEGEND:

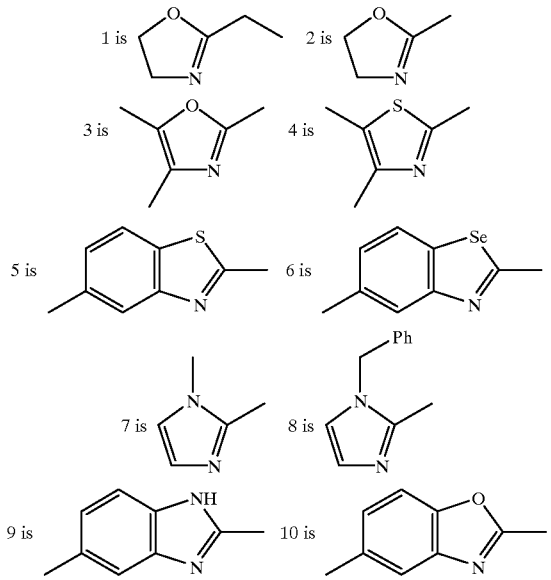

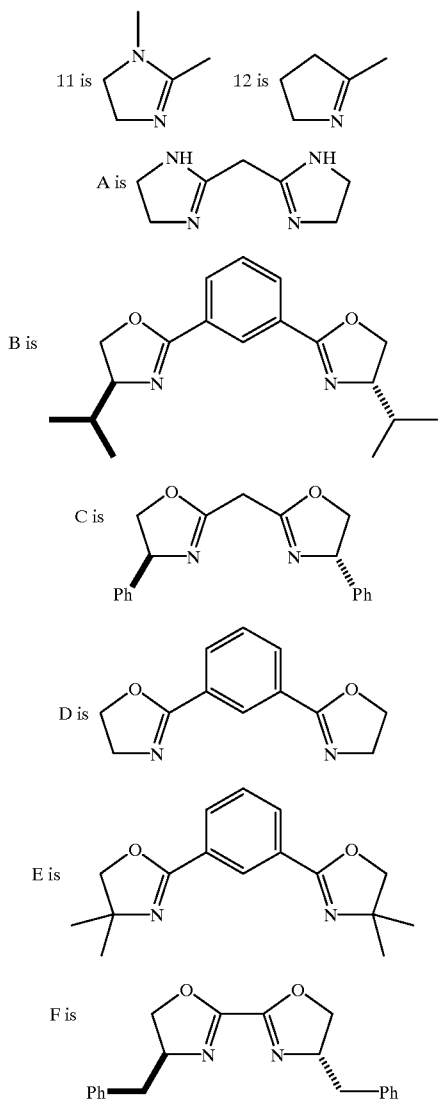

TABLE 1

| Run No. | Ligand | % Conv. | $C_3:C_5$ |
|---|---|---|---|
| 1 | A | 100 | 24 |
| 2 | B | 97 | 41 |
| 3 | C | 100 | 76 |
| 4 | 1[a] | 100 | 19 |
| 5 | 1 | 100 | 32 |
| 6 | 1[b] | 100 | 49 |
| 7 | 1[c] | 100 | 66 |
| 8[d] | 1 | 100 | 49 |
| 9 | 11 | 100 | >80 |
| 10 | 4 | 60 | >80 |
| 11 | 8 | 80 | >80 |
| 12 | 7 | 70 | 66 |
| 13 | 2 | 70 | 66 |
| 14 | 3 | <50 | 49 |
| 15 | 5 | >90 | 49 |
| 16 | 9 | 50 | 49 |
| 17 | 6 | 10 | 49 |
| 18 | D | >90 | 13 |

TABLE 1-continued

| Run No. | Ligand | % Conv. | C$_3$:C$_5$ |
|---|---|---|---|
| 19 | E | 20 | 49 |
| 20 | 12 | >80 | 99 | aOne equivalent of the promoter was used.
bFour equivalents of the promoter was used.
cTen equivalents of the promoter was used.
dThe catalyst was CuCl$_2$.

Comparative Example

No Promoter Added

The reaction was run in the same manner as that described in Example 1 with the following differences; the catalyst used was CuCl$_2$ (0.1 mmol) and no promoter was used.

After 2 hours at 100° C., no conversion of CH$_2$=CCl$_2$ was observed.

EXAMPLE 2
Reaction of CuCl and Ligand F

To a solution of 215 mg (0.67 mmol) bbbo (Legend, structure F) in 5 mL of MeCN was added 65 mg (0.66 mmol) of CuCl to give a strawberry red solution. The solution was filtered and 12 mL of Et$_2$O were added. After 20 hours, the resulting dark red crystals were filtered off, washed with Et$_2$O and dried to give 110 mg [Cu(bbbo)$_2$][CuCl$_2$]. A second crop brought the total yield to 210 mg (75%). The structure was confirmed by X-ray crystallography.

NMR Monitoring of Cu-catalyzed Addition of CCl$_4$ to Alkenes

In one series of experiments, the effect of added ligand 2-Et-2-oxazoline was investigated using trans-β-Me-styrene as the alkene substrate. After 19 hr at 80° C., CuCl gave 14% conversion to PhCH(CCl$_3$)—CHClCH$_3$ with a diastereomeric ratio (DR) of 20. With 1 equiv of ligand/Cu, conversion was 91% and the DR was 10. With 2 and 4 equiv, conversions were 96 and 100% with DRs of 9 and 7, respectively. Under similar reaction conditions, use of [Cu(bbbo)$_2$][CuCl$_2$] as catalyst gave 92% conversion with a DR of 4.5. In another experiment with 4 equiv of 2-Et-2-oxazoline/Cu, conversion was 30% after only 30 min. at 80° C.

Using trans-PhCH$_2$CH=CHCH$_3$ as the alkene substrate, a comparison of 2-Et-2-oxazoline, ethanolamine, and diethylamine ligands showed that after 1.5 hr conversions were 18, 3 and 1%, respectively.

EXAMPLE 3
Catalyst Selectivity and Lifetime Determination

These runs were done with only 0.5 mol % CuCl and a CCl$_4$/CH$_2$=CCl$_2$ ratio of one in order to differentiate promoters with respect to selectivity and lifetime. Reaction conditions: 4 mmol CCl$_4$, 4 mmol CH$_2$=CCl$_2$, 1 mL CD$_3$CN, 0.02 mmol CuCl and 0.08 mmol promoter (0.04 mmol for bidentate promoters). Reactions were heated in NMR tubes at 85° C. Results are shown in the following table.

| Run No. | Promoter | time (hr) | % conv | % C$_3$a | % C$_5$b | % C$_7$c |
|---|---|---|---|---|---|---|
| 1 | 1 | 9 | 40 | 79 | 18 | 3 |
|   |   | 36 | 86 | 71 | 23 | 6 |
|   |   | 70 | 100 | 72 | 23 | 5 |
| 2 | 2 | 9 | 47 | 84 | 16 | — |
|   |   | 36 | 72 | 92 | 8 | — |
|   |   | 70 | 100 | 88 | 12 | — |
| 3 | 10 | 9 | 4 | 67 | 23 | — |
|   |   | 36 | 74 | 84 | 14 | 2 |
|   |   | 70 | 100 | 85 | 13 | 2 |
| 4 | F | 9 | 22 | 94 | 6 | — |
|   |   | 22 | 60 | 92 | 8 | — |
|   |   | 70 | 100 | 94 | 6 | — |
| 5 | C | 9 | 20 | 84 | 14 | 2 |
|   |   | 22 | 62 | 73 | 25 | 2 |
|   |   | 70 | 100 | 77 | 20 | 3 |
| 6 | none | 72 | 97 | 80 | 18 | 2 | aC$_3$ is CCl$_3$CH$_2$CCl$_3$
bC$_5$ is CCl$_3$(CH$_2$CCl$_2$)$_2$Cl
cC$_7$ is CCl$_2$(CH$_2$CCl$_2$)$_3$Cl

Runs 1 and 5 show decreasing selectivity with indicative of limited promoter lifetime. Run 4 sustained high selectivity for 200 turnovers.

EXAMPLE 4

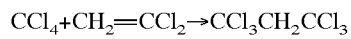
$CCl_4+CH_2=CCl_2 \rightarrow CCl_3CH_2CCl_3$

CuCl (0.1 g), 2-ethyl-2-oxazoline (0.4 g), deoxygenated CH$_3$CN (2 g), deoxygenated CCl$_4$ (16 g, 0.1 mol) and CH$_2$=CCl$_2$ (3 g, 0.031 mol) were charged into a 100 mL Pyrex® flask equipped with a Teflon® value inside a dry box. The reaction mixture was kept 80° C. After 4 hours it was analyzed by GC. The conversion of CH$_2$=CCl$_2$ was 100%, the yield of CCl$_3$CH$_2$CCl$_3$ was 92%, the selectivity of the reaction, defined as the ratio of CCl$_3$CH$_2$CCl$_3$ to CCl$_3$CH$_2$CCl$_2$CH$_2$CCl$_3$ was 97:3.

EXAMPLE 5

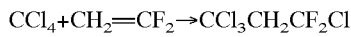
$CCl_4+CH_2=CF_2 \rightarrow CCl_3CH_2CF_2Cl$

A mixture of CCl$_4$ (52 g, 0.33 mol) CH$_3$CN (130 mL), CuCl (0.1 g) and 2-ethyl-2-oxazoline (0.4 g), prepared inside a dry box, was loaded into a 400 mL Hastelloy™ C nickel alloy shaker tube under N$_2$. The shaker tube was closed, cooled to −78° C., evacuated and CH$_2$=CF$_2$ (6.5 g, 0.1 mol) was added. The reaction mixture was kept at 130° C. for 12 hours. The shaker tube was then unloaded; the reaction mixture was washed with water twice to remove CH$_3$CN, dried over P$_2$O$_5$ and the crude reaction mixture (40 g) analyzed by GC and $^1$H and $^{19}$F NMR. The yield of CCl$_3$CH$_2$CF$_2$Cl was 70%, the selectivity of the reaction based on converted olefin was 81%.

EXAMPLE 6

$CCl_4+CHF=CF_2 \rightarrow C_3HCl_4F_3$

Example 5 was repeated using the same amounts of reagents except that CHF=CF$_2$ (8 g, 0.1 mol) was used instead of CH$_2$=CF$_2$. The isolated product (41 g) contained, based on $^1$H, $^{19}$F NMR and GC, CCl$_4$ (51%), C$_3$Cl$_4$F$_3$H (29%, two isomers in a 7:3 ratio), C$_5$Cl$_4$F$_6$H$_2$ (8%, mixture of isomers) and CH$_3$CN (12%). The yield of isomeric propanes was 62%, the selectivity based on converted olefin was 60%.

EXAMPLE 7

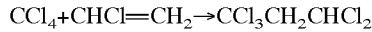
$CCl_4+CHCl=CH_2 \rightarrow CCl_3CH_2CHCl_2$

Example 5 was repeated using the same amounts of reagents except that CHCl=CH$_2$ (7 g, 0.1 mol) was used instead of $CH_2=CF_2$. The isolated product (54 g) contained, based on $^1H$, $^{19}F$ NMR and GC, $CH_3CN$, $CCl_4$, $CCl_3CH_2CHCl_2$ and a small amount of $CCl_3(CH_2CHCl)_nCl$ (n=2 and 3). The yield of $CCl_3CH_2CHCl_2$ was 69%, the selectivity based on converted olefin was 64%.

EXAMPLE 8

$CCl_4+CH_3CH=CH_2 \rightarrow CCl_3CH_2CHClCH_3$

Example 5 was repeated using the same amounts of reagents except that propylene (5 g, 0.1 mol) was used instead of $CH_2=CF_2$. The isolated product (54 g) contained, based on $^1H$, $^{19}F$ NMR and GC, $CH_3CN$, $CCl_4$, $CCl_3CH_2CHClCH_3$. The yield of $CCl_3CH_2CHClCH_3$ was 95%, the selectivity based on converted olefin was >95%.

EXAMPLE 9

$CCl_4+CF_2=CF_2 \rightarrow CCl_3CF_2CF_2Cl$

Example 5 was repeated using the same amounts of reagents except that tetrafluoroethylene (10 g, 0.1 mol) was used instead of $CH_2=CF_2$. The isolated product (45 g) contained, based on $^{19}F$ NMR and GC, $CCl_4$ (66.5%), $CCl_3CF_2CF_2Cl$ (23%), $CCl_3(CF_2CF_2)_2Cl$ (6%), $CCl_3(CF_2CF_2)_3Cl$ (2.6%), $CCl_3(CF_2CF_2)_4Cl$ (1.4%), $CCl_3(CF_2CF_2)_5Cl$ (0.6%). The yield of $CCl_3CF_2CF_2Cl$ was 40%, the selectivity based on converted olefin was 65%.

EXAMPLE 10

$CCl_3CF_3+CH_2=CH_2 \rightarrow CF_3CCl_2CH_2CH_2Cl$

Example 5 was repeated using the same amounts of reagents except that ethylene (4 g, 0.1 mol) and $CCl_3CF_3$ (60 g, 0.3 mol) were used instead of $CH_2=CF_2$ and $CCl_4$. The isolated product (45 g) contained, based on $^{19}F$ NMR and GC, $CCl_3CF_3$ (60%), $CF_3CCl_2CH_2CH_2Cl$ (20%), $CF_3CCl_2(CH_2CH_2)_2Cl$ (10%), $CF_3CCl_2(CH_2CH_2)_3Cl$ (2%) and $CH_3CN$ (8%). The yield of $CF_3CCl_2CH_2CH_2Cl$ was 70%, the selectivity based on converted olefin was 63%.

What is claimed is:

1. A liquid phase process for producing halogenated alkane adducts of the formula $CAR^1R^2CBR^3R^4$ wherein $R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl, provided that only two of $R^1$, $R^2$, $R^3$, and $R^4$ can be selected from $C_1$–$C_6$ alkyl, CN, $CO_2CH_3$, $CH_2Cl$, and aryl;

A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$, each X is independently selected from the group consisting of Br, Cl and I, a is an integer from 0 to 3, n is an integer from 1 to 6, b is an integer from 1 to 2n+1, and c is an integer from 0 to 1; and B is selected from the group consisting of Br, Cl and I;

provided that (1) when A is $CX_3$ then only one of X is I, (2) when A is $CH_{3-a}X_a$ then each X is B and a is an integer from 1 to 2 when B is Br, a is 2 when B is Cl, and a is an integer from 0 to 2 when B is I, and (3) when A is $C_nH_{(2n+1)-b}X_b$ then each X is independently selected from Cl and F and B is I, comprising:

contacting a halogenated alkane of the formula AB with an olefin of the formula $CR^1R^2=CR^3R^4$ in the presence of a catalyst system containing (i) at least one catalyst selected from the group consisting of monovalent and divalent copper, and (ii) at least one promoter selected from the group consisting of pyridazines, pyrazines, and aliphatic heterocyclic compounds which contain at least one carbon-nitrogen double bond in the heterocyclic ring.

2. A liquid phase process for producing halogenated alkane adducts of the formula $CAR^1R^2CBR^3R^4$ wherein $R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl, provided that only two of $R^1$, $R^2$, $R^3$, and $R^4$ can be selected from $C_1$–$C_6$ alkyl, CN, $CO_2CH_3$, $CH_2Cl$, and aryl;

A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$, each X is independently selected from the group consisting of Br, Cl and I, a is an integer from 0 to 3, n is an integer from 1 to 6, b is an integer from 1 to 2n+1, and c is an integer from 0 to 1; and B is selected from the group consisting of Br, Cl and I;

provided that (1) when A is $CX_3$ then only one of X is I, (2) when A is $CH_{3-a}X_a$ then each X is B and a is an integer from 1 to 2 when B is Br, a is 2 when B is Cl, and a is an integer from 0 to 2 when B is I, and (3) when A is $C_nH_{(2n+1)-b}X_b$ then each X is independently selected from Cl and F and B is I, comprising:

contacting a halogenated alkane of the formula AB with an olefin of the formula $CR^1R^2=CR^3R^4$ in the presence of a catalyst system containing (i) at least one catalyst selected from the group consisting of monovalent and divalent copper, and (ii) at least one promoter selected from the group consisting of imidazoles, imidazolines, oxadiazoles, oxazoles, oxazolines, isoxazoles, thiazoles, thiazolines, pyrrolines, trihydropyrimidines, pyrazoles, triazoles, triazolium salts, isothiazoles, tetrazoles, tetrazolium salts, thiadiazoles, pyridazines, pyrazines, oxazines and dihydrooxazine.

3. A liquid phase process for producing halogenated alkane adducts of the formula $CAR^1R^2CBR^3R^4$ wherein $R^1$, $R^2$, $R^3$, and $R^4$ are each independently selected from the group consisting of H, Br, Cl, F, $C_1$–$C_6$ alkyl, CN, $CO_2CH_3$, $CH_2Cl$, and aryl, provided that only two of $R^1$, $R^2$, $R^3$, and $R^4$ can be selected from $C_1$–$C_6$ alkyl, CN, $CO_2CH_3$, $CH_2Cl$, and aryl;

A is selected from the group consisting of $CX_3$, $CH_{3-a}X_a$, $C_nH_{(2n+1)-b}X_b$ and $CH_cX_{2-c}R$, where R is $C_nH_{(2n+1)-b}X_b$, each X is independently selected from the group consisting of Br, Cl and I, a is an integer from 0 to 3, n is an integer from 1 to 6, b is an integer from 1 to 2n+1, and c is an integer from 0 to 1; and B is selected from the group consisting of Br, Cl and I;

provided that (1) when A is $CX_3$ then only one of X is I, (2) when A is $CH_{3-a}X_a$ then each X is B and a is an integer from 1 to 2 when B is Br, a is 2 when B is Cl, and a is an integer from 0 to 2 when B is I, and (3) when A is $C_nH_{(2n+1)-b}X_b$ then each X is independently selected from Cl and F and B is I, comprising:.

contacting a halogenated alkane of the formula AB with an olefin of the formula $CR^1R^2=CR^3R^4$ in the presence of a catalyst system containing (i) at least one catalyst selected from the group consisting of monovalent and divalent copper, and (ii) at least one promoter selected from the group having the Formula (I) or Formula (II)

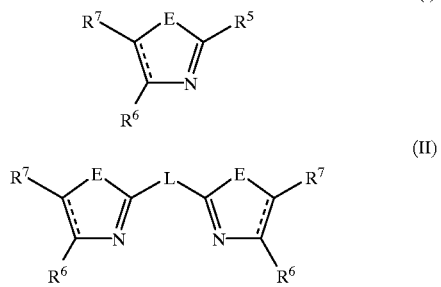

wherein E is selected from the group consisting of —O—, —S—, —Se—, —$CH_2$—, and —$N(R^8)$—; $R^5$ is selected from the group consisting of $CH_3$ and $C_2H_5$; $R^6$ and $R^7$ are selected from the group consisting of H, $CH_3$, $C_6H_5$, $CH_2C_6H_5$, $CH(CH_3)_2$, and fused phenyl; L is selected from the group consisting of —O—, —S—, —Se—, —$N(R^8)$—, —$C_6H_4$—, 2,6-pyridyl, —$OC_6H_4$—$C_6H_4O$—, —$CH_2CH_2OCH_2CH_2$—, and —$(CH_2)_p$— where p is an integer from 0 to 6; and each $R^8$ is selected from the group consisting of H and $C_mH_{2m+1}$ where m is an integer from 1 to 6.

4. The process of claim 1 wherein the promoter is selected from the group consisting of aliphatic heterocyclic compounds which contain at least one carbon-nitrogen double bond in the, heterocyclic ring.

5. The process of claim 4 wherein the halogenated alkane is selected from the group consisting of $CBrCl_3$, $CBrF_3$, $CCl_4$, $CCl_3F$, $CCl_2F_2$, $CF_3I$, $CCl_2FCCl_2F$, $CCl_3CF_3$, $CCl_3CF_2CF_3$, $CCl_3CH_2CCl_3$, $CF_3CF_2I$, $CF_3CF_2CF_2I$, $CCl_3CH_2CF_3$, and $CCl_3(CF_2CF_2)_qCl$ where q is an integer from 1 to 6.

6. The process of claim 5 wherein the olefin is selected from the group consisting of $CF_2$=$CF_2$, $CF_2$=$CClF$, $CF_2$=$CCl_2$, $CClF$=$CClF$, $CClF$=$CCl_2$, $CF_2$=$CHF$, $CF_2$=$CH_2$, $CHF$=$CHF$, $CHF$=$CH_2$, $CH_2$=$CH_2$, $CH_2$=$CHCH_3$, $CH_2$=$CHCF_3$, $CH_2$=$CFCF_3$, $CH_2$=$CHCl$, $CH_2$=$CCl_2$, $CHCl$=$CHCl$, $CHCl$=$CCl_2$, $CH_2$=$CHCl$, $CH_2$=$CHCH_2Cl$, $CH_2$=$CHAryl$, $CH_2$=$CHCO_2CH_3$, $CH_2$=$C(CH_3)CO_2CH_3$, $CH_2$=$CHCO_2C_2H_5$, and $CH_2$=$C(CH_3) CO_2C_2H_5$.

7. The process of claim 4 wherein the copper catalyst is selected from the group consisting of copper(I) chloride, copper(II) chloride, copper(I) bromide, copper(II) bromide, copper(I) iodide, copper(II)acetate and copper(II) sulfate.

8. The process of claim 4 where the reaction is done in the presence of a solvent selected from the group consisting of acetonitrile, dimethyl sulfoxide, dimethyl formamide, tetrahydrofuran, isopropanol, t-butanol, polyethers of the formula $R^9O(CH_2CH_2O)_rR^9$ where each $R^9$ is independently selected from the group consisting of H, $CH_3$ and $C_2H_5$ and r is an integer from 1 to 4, esters of the formula $R^{10}CO_2R^{10}$ where each $R^{10}$ is independently selected from $C_1$–$C_6$ alkyl groups and mixtures thereof.

9. The process of claim 8 wherein the solvent is acetonitrile.

10. The process of claim 4 wherein the reaction is accomplished in a homogenous system.

11. The process of claim 4 wherein the promoter is selected from the group consisting of imidazoles, imidazolines, oxadiazoles, oxazoles, oxazolines, isoxazoles, thiazoles, thiazolines, pyrrolines, trihydropyrimidines, pyrazoles, triazoles, triazolium salts, isothiazoles, tetrazoles, tetrazolium salts, thiadiazoles, oxazines and dihydrooxazine.

12. The process of claim 1 wherein the halogenated alkane is selected from the group consisting of $CBrCl_3$, $CBrF_3$, $CCl_4$, $CCl_3F$, $CCl_2F_2$, $CF_3I$, $CCl_2FCCl_2F$, $CCl_3CF_3$, $CCl_3CF_2CF_3$, $CCl_3CH_2CCl_3$, $CF_3CF_2I$, $CF_3CF_2CF_2I$, $CCl_3CH_2CF_3$, and $CCl_3(CF_2CF_2)_qCl$ where q is an integer from 1 to 6.

13. The process of claim 12 wherein the olefin is selected from the group consisting of $CF_2$=$CF_2$, $CF_2$=$CClF$, $CF_2$=$CCl_2$, $CClF$=$CClF$, $CClF$=$CCl_2$, $CF_2$=$CHF$, $CF_2$=$CH_2$, $CHF$=$CHF$, $CHF$=$CH_2$, $CH_2$=$CH_2$, $CH_2$=$CHCH_3$, $CH_2$=$CHCF_3$, $CH_2$=$CFCF_3$, $CH_2$=$CHCl$, $CH_2$=$CCl_2$, $CHCl$=$CHCl$, $CHCl$=$CCl_2$, $CH_2$=$CHCl$, $CH_2$=$CHCH_2Cl$, $CH_2$=$CHAryl$, $CH_2$=$CHCO_2CH_3$, $CH_2$=$C(CH_3)CO_2CH_3$, $CH_2$=$CHCO_2C_2H_5$, and $CH_2$=$C(CH_3) CO_2C_2H_5$.

14. The process of claim 1 wherein the copper catalyst is selected from the group consisting of copper(I) chloride, copper(II) chloride, copper(I) bromide, copper(II) bromide, copper(I) iodide, copper(II) acetate and copper(II) sulfate.

15. The process of claim 3 wherein the promoter is a promoter of Formula II which is optically active.

16. The process of claim 1 where the reaction is done in the presence of a solvent selected from the group consisting of acetonitrile, dimethyl sulfoxide, dimethyl formamide, tetrahydrofuran, isopropanol, t-butanol, polyethers of the formula $R^9O(CH_2CH_2O)_rR^9$ where each $R^9$ is independently selected from the group consisting of H, $CH_3$ and $C_2H_5$ and r is an integer from 1 to 4, esters of the formula $R^{10}CO_2R^{10}$ where each $R^{10}$ is independently selected from $C_1$–$C_6$ alkyl groups and mixtures thereof.

17. The process of claim 16 wherein the solvent is acetonitrile.

18. The process of claim 1 wherein the reaction is accomplished in a homogenous system.

19. A process for producing a hydrofluoroalkane comprising:

(a) producing a hydrochlorofluoroalkane by reacting AB and $CR^1R^2$=$CR^3R^4$ in accordance with the process of claim 1, provided that B and X are Cl and at least one of AB and $CR^1R^2$=$CR^3R^4$ contain hydrogen; and (b) reacting the hydrochlorofluoroalkane produced in (a) with HF.

* * * * *